United States Patent [19]

Popson et al.

[11] Patent Number: 5,260,584

[45] Date of Patent: Nov. 9, 1993

[54] INSTRUMENT FOR MEASURING REFLECTIVE PROPERTIES OF PAPER AND OTHER OPAQUE MATERIALS

[75] Inventors: Stephen J. Popson, New Albany; Kenneth A. Richey, Pekin, both of Ind.

[73] Assignee: Technidyne Corporation, New Albany, Ind.

[21] Appl. No.: 911,501

[22] Filed: Jul. 10, 1992

[51] Int. Cl.⁵ ............................................. G01N 21/86
[52] U.S. Cl. ...................................... 250/571; 250/226; 356/448
[58] Field of Search .................... 250/571, 226, 223 R; 356/445, 446, 447, 448

[56] References Cited

U.S. PATENT DOCUMENTS

| | | | |
|---|---|---|---|
| 4,761,676 | 8/1988 | Wiles et al. | 356/445 |
| 5,021,645 | 6/1991 | Satula et al. | 250/226 |
| 5,150,174 | 9/1992 | Ryczek et al. | 356/446 |

FOREIGN PATENT DOCUMENTS 3026439  2/1982  Fed. Rep. of Germany .
1396008  5/1988  U.S.S.R. .

Primary Examiner—David C. Nelms
Attorney, Agent, or Firm—Maurice L. Miller, Jr.

[57] ABSTRACT

A portable, hand held reflectometer which employs at least one blue light emitting diode for measuring the optical brightness of an opaque material, such as a stack or pad of paper is disclosed. A brightness measuring reflectometer which employs two blue light emitting diodes arranged so as to substantially reduce measured brightness variations caused by changing the orientation of the reflectometer relative to that of the fibers contained in a fibrous material such as paper whose brightness is to be measured is also disclosed. An ultraviolet light source such as a fluorescent lamp is also employed for measuring the brightness of paper or other materials which contain ultraviolet light excitable blue wavelength emitting substances. An electronic circuit for operating the reflectometer is also disclosed which employs a negative feedback circuit for maintaining the intensity of the ultraviolet light source at a relatively constant level.

32 Claims, 3 Drawing Sheets

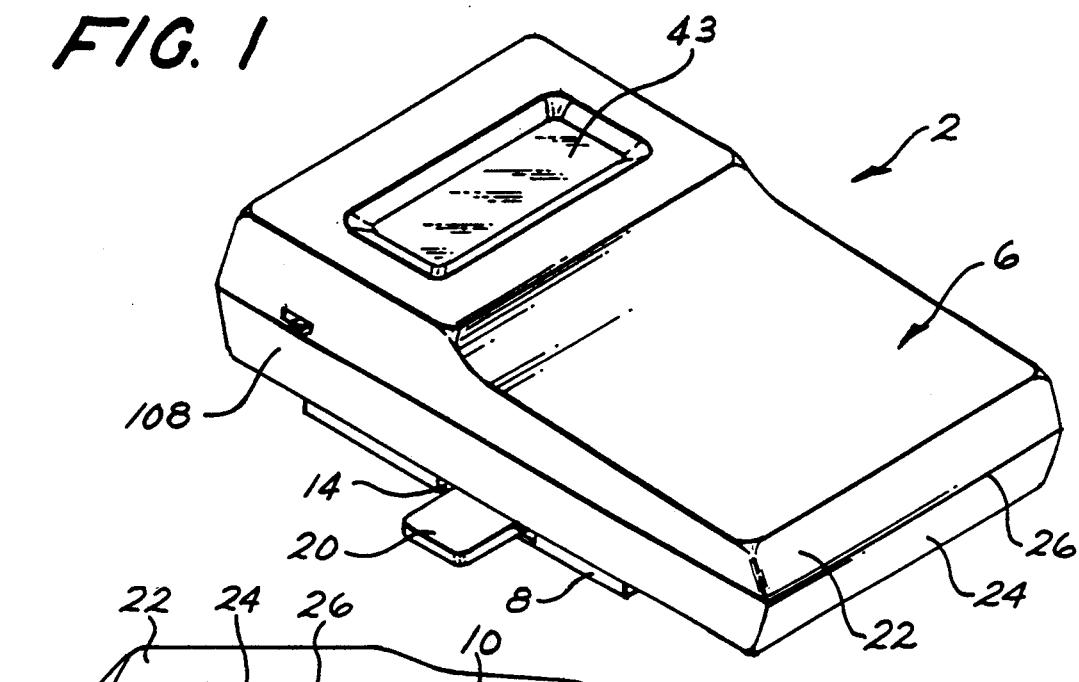
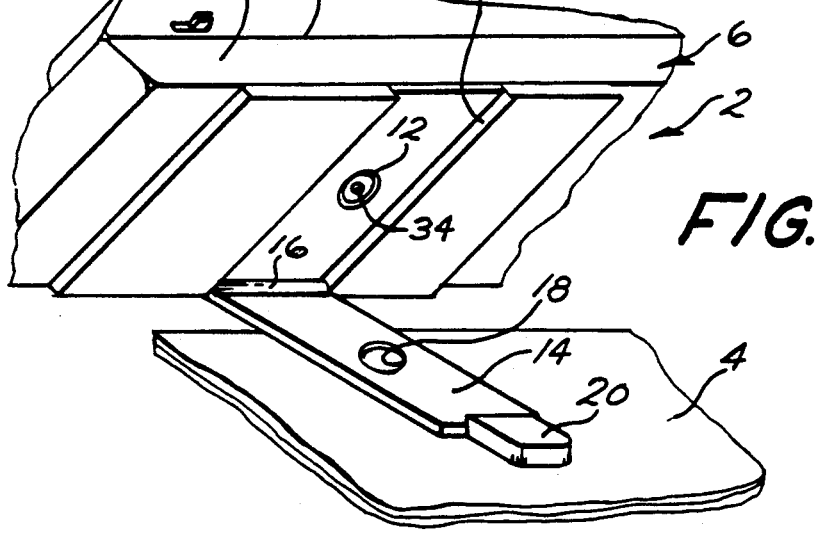
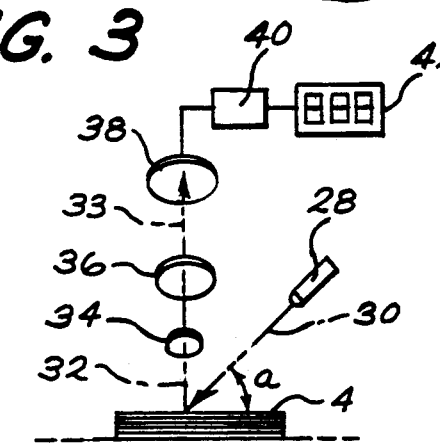
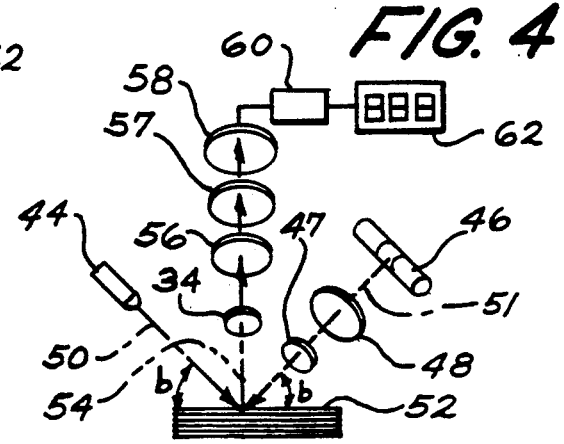

INSTRUMENT FOR MEASURING REFLECTIVE PROPERTIES OF PAPER AND OTHER OPAQUE MATERIALS

BACKGROUND OF THE INVENTION

This invention relates generally to a reflectometer of the type used to measure certain optically reflective properties of opaque materials. More specifically, the invention relates to a portable, hand held reflectometer which utilizes at least one blue light emitting diode to measure the brightness of paper products. The invention also relates to a paper brightness measuring reflectometer which employs two separate blue light sources of any suitable type arranged so as to substantially reduce measured paper brightness variations caused by changing the orientation of the instrument relative to that of the fibers in the paper whose brightness is being measured.

Broadly speaking, surface reflectance meters have long been known and used in the prior art in a wide range of applications to control the appearance quality of manufactured goods according to set standards and/or purchaser specifications. For example, manufacturers often wish to control the gloss and color characteristics of products having painted surfaces. Magazine and newspaper publishers often desire to purchase paper from paper manufacturers for use in their periodicals according to selected specifications of brightness, as do producers of high quality bond paper such as is used for letterhead. Book publishers are yet another example of paper users who often desire to purchase paper according to selected specifications of appearance. In this way, appearance of the paper in a given book can be maintained from page to page, as well as the appearance of the paper from one book copy to the next in a given printing, as well as the appearance of the paper in the books of different printings, even where such printings occur years apart.

One prior art reflectometer device which is adapted to measure the "gloss" of a painted surface is disclosed in U.S. Pat. No. 4,761,676 issued to G. R. Wiles et al. on Aug. 2, 1988. This device is a portable system which employs an infrared light emitting diode to generate a collimated light beam which is passed, first, through a stationary diffuser and, then, through a rotary light chopper removably disposed in the light beam path, to be focused as a spot of light on the surface whose gloss is to be measured. Light reflected from the surface passes through an imaging lens, thence through a device containing a light slit onto a first photodetector. The rotary chopper contains a series of light chopper blades which periodically interrupt the light beam. One of these blades contains a synchronization mirror which, once during each rotation of the chopper, reflects light from the light emitting diode to a second photodetector. The light signals received by each of these photodetectors are converted to electrical impulse signals which are fed to an electrical signal processor. Upon removal of the light chopper from the light beam path, the processor determines the time rate of change of light flux falling on the first photodetector by measuring the time it takes for reflected light falling thereon to increase from a first to a second predetermined level, which is indicative of the degree of gloss of the surface.

The subject reflectometer, while utilizing light reflected from a sample, is relatively complex and employs moving parts in the operation thereof. Also, it is not adapted to measure the surface reflectance property of brightness, with which the present invention is concerned. Finally, it does not contain a blue light emitting diode essential to an important aspect of the present invention.

Hand held optical photometers which detect light reflected from a test strip inserted therein, which strip serves as a calibration standard, are also known in the prior art. See German Patent No. DE 3026439 A1 published Feb. 11, 1982. So, too, have methods for measuring the quality and composition of substances, materials and coatings, by measuring the brightness of light reflected from a sample at a specific angle, long been known in the prior art. See, for example, Russian Pat. No. SU 1396008 A1. So, too, have portable, hand held photometers for measuring the color of painted surfaces which direct a broad band optical light beam (white light) onto a sample and detect the reflected light from the sample with blue enhanced silicon photodiode receiving devices been known and used in this country as exemplified by the X-Rite 918 Tri Stimulous Colorimeter manufactured by X-Rite of 3100 44th Street S.W., Grandville, Mich. 49418.

Finally, fixed, non-portable brightness testers, which use a blue wavelength filter in association with a broad spectrum light beam generating device (a "white light" generator), and which detect the magnitude of blue light reflected from a sample pad of paper at a selected angle relative to the incident light beam focused on the pad, have long been known and used in the prior art. Such prior art testers have also employed an ultraviolet light generator ("black light" generator), such as a fluorescent or xenon lamp, in addition to a white light generator in the measurement of brightness. But these testors are large and heavy and therefore must be operated from fixed platforms because their optical systems are bulky and heavy. Also, a great deal of power is consumed in their light beam generating systems. It is also necessary to fix the orientation of such brightness testers relative to the alignment of the paper fibers, because changes in this orientation cause substantial changes in the brightness of the paper as sensed by the tester.

By means of our invention, these and other difficulties encountered with prior art reflectometers used in measuring the brightness of opaque materials, such as paper, are substantially overcome.

SUMMARY OF THE INVENTION

It is an object of our invention to provide a reflectometer for measuring the brightness of an opaque material whose optical system is substantially reduced in size, weight and power requirements as compared with prior art reflectometers so as to be light in weight, highly portable, and battery operated.

It is another object of our invention to provide a reflectometer for the measurement of brightness which utilizes, as at least one light source, a blue light emitting diode.

It is yet another object of our invention to provide a portable reflectometer for the measurement of the brightness of paper and other fibrous materials which employs two separate blue light sources, wherein the magnitude of the brightness sensed by the reflectometer is substantially independent of the orientation of the reflectometer on the paper relative to the orientation of the paper fibers.

Briefly, in accordance with our invention, there is provided a reflectometer for measuring optical brightness of an opaque material which includes a housing having a flat surface member defining an aperture for the uninterrupted passage of a collimated light beam therethrough. An aperture defining portion of the member is adapted for placement flush against a surface of a material whose brightness is to be measured. A blue wavelength visible light emitting diode is disposed in the housing so as to direct a collimated beam of blue light through the aperture onto the material at a first preselected angle relative to a plane parallel to the flat aperture defining portion of the member. Means is disposed in the housing for receiving the portion of the light beam which is reflected through the aperture from the material at a second preselected angle relative to the plane, one of the preselected angles being essentially ninety degrees and the other being greater than zero and less than ninety degrees. Lastly, means is responsively connected to the receiving means for sensing the magnitude of the reflected portion of the light beam relative to a predetermined standard.

These and other objects, features and advantages of our invention will become apparent to those skilled in the art from the following detailed description and attached drawings upon which, by way of example, only the preferred embodiments of our invention are described and shown.

BRIEF DESCRIPTION OF THE DRAWINGS

FIG. 1 shows a perspective view of a portable, hand held reflectometer for use in measuring the brightness of an opaque material such as paper, paper board and the like, thus illustrating a preferred embodiment of our invention.

FIG. 2 shows a perspective view of a fragment of the underside of the reflectometer of FIG. 1 illustrating the use of a hingable, aperture defining member to position the reflectometer to measure the brightness on a selected surface portion of a stack of paper.

FIG. 3 shows, schematically, one example of an optical system that may be employed in the reflectometer of FIG. 1.

FIG. 4 shows, schematically, another example of an optical system that may be employed in the reflectometer of FIG. 1.

DESCRIPTION OF THE PREFERRED EMBODIMENT

Figure 5:
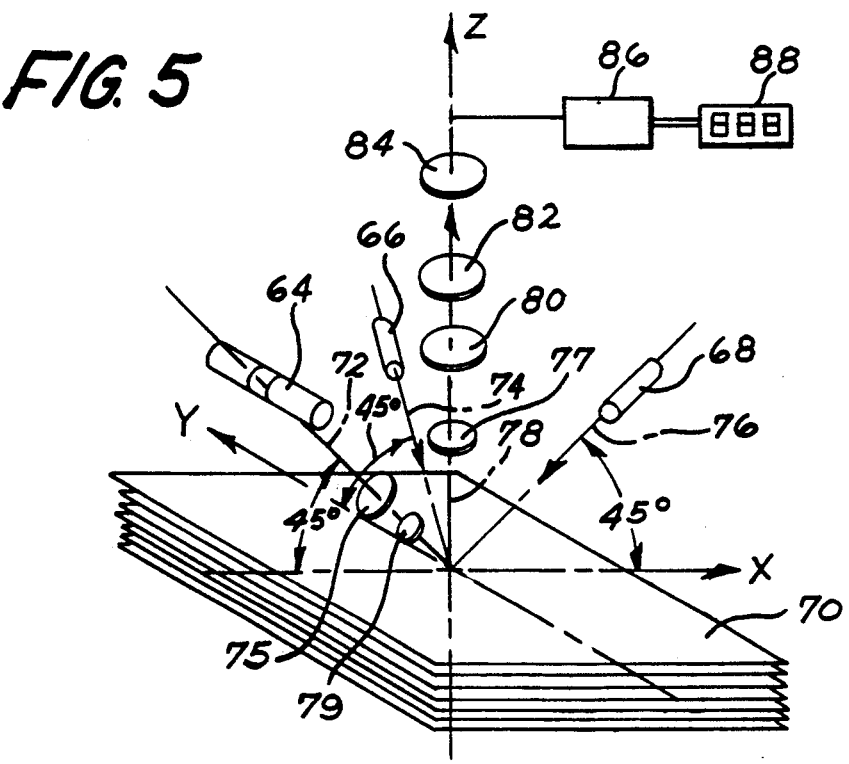
FIG. 5 shows, schematically, yet another example of an optical system that may be employed in the reflectometer of FIG. 1.

Referring now to the drawing figures and, in particular, to FIGS. 1-2, there is shown, in one preferred embodiment of our invention, a portable reflectometer device 2 of the hand held type for use in measuring the optical brightness of an opaque material such as, for example, a stack or pad of paper 4 (FIG. 2). The device 2 includes a housing 6 which may be constructed of molded plastic or other suitable material having a base plate 8 which contains an elongated channel 10, in the center of which is a circular opening 12 which communicates with the interior of the housing 6. A relatively flat rectangular strip or member 14 is hingably connected in any suitable manner on one end 16 thereof to the plate 8 so as to lie within the channel 10 in relatively tight, friction fitting relationship therewith when in a closed position as shown in FIG. 1, and which is tiltable out of the channel 10 as desired as shown in FIG. 2. The member 14 defines an aperture 18 which registers with the opening 12 when the member 14 is closed against the base plate 8 within the channel 10. A finger tab 20 is attached to a free end of the member 14 and projects beyond one side of the housing 6 when the member 14 is closed against the base plate 8 as shown in FIG. 1 to provide means for manual manipulation of the tiltable member 14. The housing 6 includes a pair of removably attached covers 22 and 24 which slip fit together to form a seam 26, and which can be pulled apart by hand to provide access to the interior of the housing 6 as necessary.

Referring also to FIG. 3 to illustrate one example of the optics of the invention, the device 2 also includes a blue wavelength visible light emitting diode or blue LED 28 which is disposed in the housing 6 so as to direct a collimated beam of blue light 30 through the opening 12 in the base plate 8 and through the aperture 18 of the member 14 when the latter is in the closed position, onto the paper pad 4 whose brightness is to be measured and upon which the device 2 is placed. In the example shown in FIG. 3, the LED 28 is positioned in the housing 6 so as to direct the blue light beam 30 through the opening 12 and aperture 18 at a first preselected angle a relative to the surface of the pad 4, i.e. relative to a plane parallel to the abutting surfaces of the pad 4 and member 14. While the angle a is preferably 45 degrees in accordance with long accepted industry standards, it may be any suitable angle between zero and ninety degrees so long as the light beam 30 can be directed in an uninterrupted manner through the opening 12 and aperture 18 to form a spot of light on the surface of the pad 4. As a practical matter, the combined thickness of the opening defining portion of the plate 8 and the aperture defining portion of the member 14 and the distance back from the opening 12 that the LED 28 is placed within the housing 6, will limit the minimum angle a at which the beam 30 can be directed from the LED 28 onto the pad 4 without interference. In accordance with the present example, a portion 32 of the incident light beam 30 striking the pad 4 will be reflected in a direction normal to a plane which is parallel to the member 14 when in its closed position in the channel 10 and when lying flush against the pad 4. The reflected portion 32 is directed through a focal lens 34 (FIGS. 2-3), thence through an optical filter 36 which is transparent to a very narrow band of light in the blue wavelength optical region, but which is otherwise opaque, and strikes a receiving means 38 such as a silicon photodetector. The photodetector 38 thus generates an electrical output signal whose amplitude is directly proportional to the reflected and filtered light beam portion 33 which strikes it. This electrical signal is then suitably amplified by an amplifier 40 which is, in turn, attached to a suitable register 42, which can be viewed through a display window 43 (FIG. 1).

Referring now to FIGS. 1-2 and 4, many types of paper contain materials which fluoress when excited by ultraviolet light, which action tends to enhance the apparent brightness of the paper. In order to measure the apparent brightness of such paper, a suitable ultraviolet light generator is employed in the brightness tester along with a blue light generator. Such an optical system for use in the reflectometer of FIG. 1 is shown schematically in FIG. 4, and includes a blue light emitting diode 44, a fluorescent lamp 46, a suitable focal lens 47, and a filter 48 which is transparent to ultraviolet light, but which is otherwise opaque, and which is disposed in a path 51 of the incident ultraviolet light beam. Both the blue LED 44 and the fluorescent lamp 46 are placed in the housing 6 (FIG. 1-2) so as to direct their respective collimated light beams 50 and 51 through the opening 12 and aperture 18 (FIG. 2) to form a single light spot on a paper pad 52. Each of the radiation beams 50 and 51 impinge upon the surface of a paper pad 52 at a first preselected angle b of, preferably, 45 degrees, although these two angles need not necessarily be equal to one another. The resulting reflected portion 54 of the beams 50 and 51, which is reflected normal to the pad 52, is then passed through the lens 34 (FIG. 2), a blue filter 56, an ultraviolet light limiting filter 57, and is directed onto a silicon photodetector 58. The corresponding electrical output signal of the photocell 58 is then suitably amplified by an amplifier and processor 60, an output signal of which operates a suitable register 62 located in the housing 6 and viewable through the display window 43, indicative of brightness of the paper pad 4.

Now with reference to FIGS. 1-2 and 5, it is well known in the paper industry, that the orientation of the fibers in a sample pad of paper whose brightness is to be measured relative to the direction of the incident blue light beam, as measured along the pad, will have a substantial effect upon the apparent brightness of the sample as measured. This is true in the case of all prior art reflectometers which utilize only a single blue light source and is also true of the reflectometer of the two previous examples of the present invention, both of which examples employ only a single blue LED. The direction in which the elongated paper fibers extend in a given sample of paper is referred to as the "machine" direction and the direction along the surface of the paper which is perpendicular to the machine direction is referred to as the "cross-machine" direction. The apparent brightness of paper as measured by a reflectometer having a single blue light beam source will be greater when the direction of incident blue light beam along the plane of the paper is perpendicular to the longitudinal direction of the paper fibers (the cross machine direction) than will be the case when oriented parallel to the machine direction. Moreover, the apparent brightness, as so measured, will vary with the changes in the orientation of the paper and, consequently with changes in the orientation of the paper fibers, relative to the direction of the blue light beam as measured parallel to the paper, between these two extremes, i.e. between the machine and cross machine directions.

Figure 6:
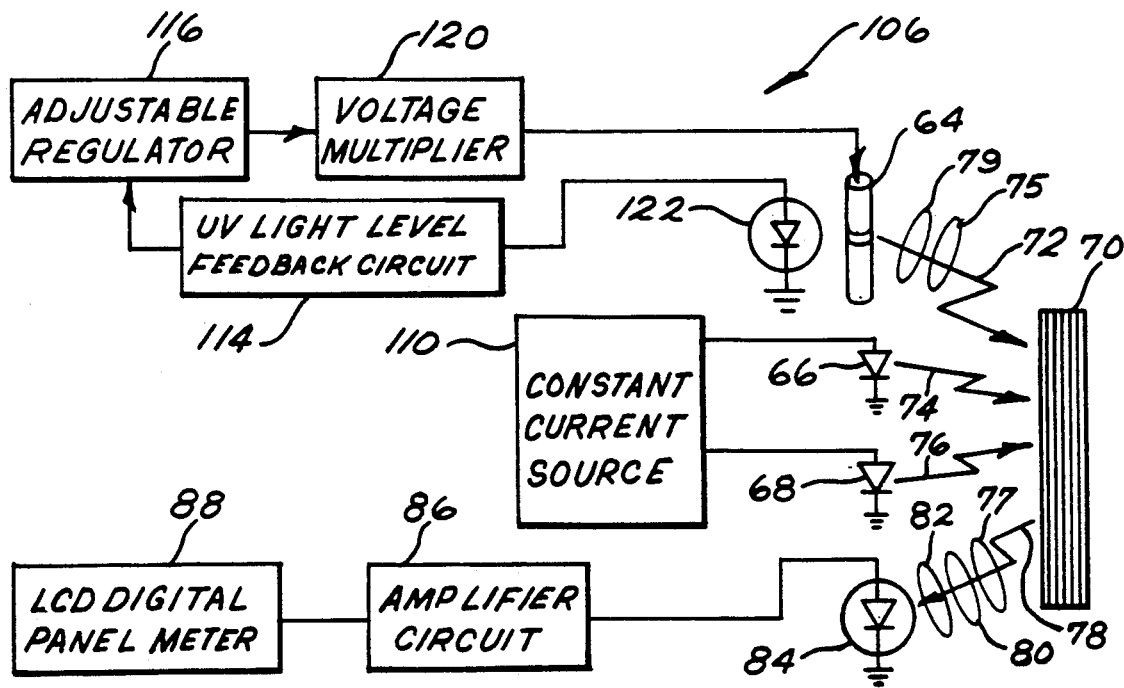
FIG. 6 shows a block diagram of the electronic logic of the reflectometer of FIG. 1 using the optical system of FIG. 5.
Figure 7:
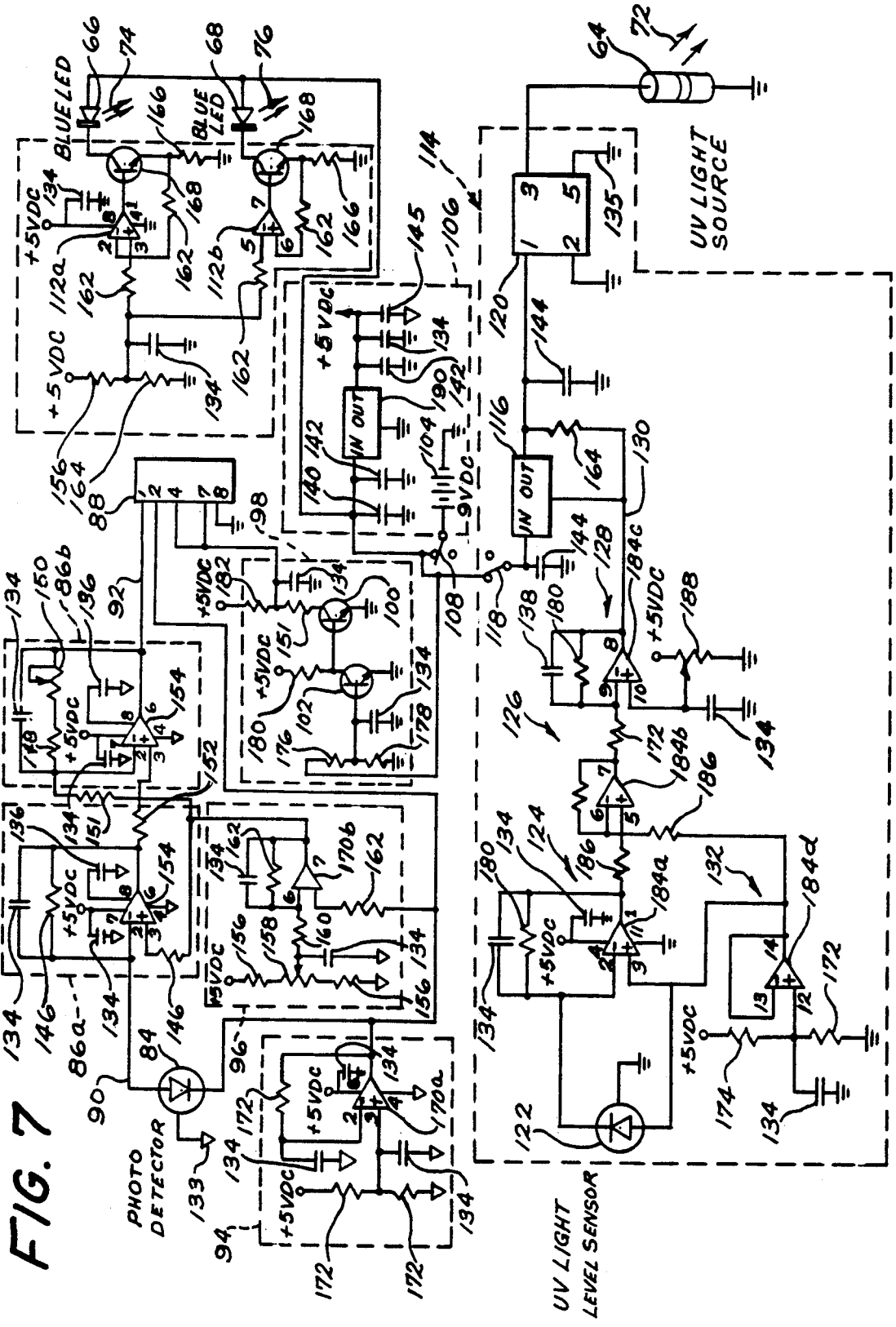
FIG. 7 shows a circuit diagram for the electronics of the reflectometer of FIG. 1 according to the example illustrated in FIGS. 5-6.

To substantially reduce such variations caused by changes in orientation of the paper fibers relative to that of the brightness tester, we provide a preferred embodiment of the invention as exemplified in FIGS. 5-7, whose optical system is shown schematically in FIG. 5. The subject optical system includes a suitable ultraviolet light source 64 and two separate blue light sources 66 and 68 of any suitable type. We, of course, prefer to use two blue LED's as the blue light sources 66 and 68 in order to save size, space, and power consumption and so that the system can be employed in a small, light weight, hand held, battery operated unit adaptable for use in the housing 6 of FIGS. 1-2, but this is not essential. The sources 64, 66 and 68 are each disposed in the housing 6 of the instrument of FIG. 1 so as to direct three incident, collimated radiation beams 72, 74 and 76 respectively, through the opening 12 and aperture 18 (FIG. 2), onto the surface of a pad 70 of paper to form a single light spot thereon. The preselected angles which the incident beams 72, 74 and 76 make with the plane of the pad 70 are equal to one another and, in present example, conform to the paper industry standard, which is 45 degrees. A filter 75, which is transparent with respect to ultraviolet light but which is otherwise opaque, is disposed in the UV light beam 72. A portion 78 of the resulting light, which is reflected normal to the plane containing the pad 70, is passed through a focal lens 77, an ultraviolet light absorbing filter 80 which is otherwise transparent, and a blue wavelength transmitting filter 82, similar to the filter 56 of the previous example, although the order of placement of the filters 77, 80 and 82 is not critical and can be modified as desired. The reflected light portion 78, as thus filtered, impinges upon a photodetector 84 to produce a corresponding electrical signal which is presented to a suitable amplifier and processor 86 which is, in turn, connected to a suitable register 88 such as one of the liquid crystal type. The blue light sources 66 and 68 are arranged in the housing 6 relative to one another such that the directions of their light beam components which are parallel to the surface 70 are rotationally displaced essentially 90 degrees from one another as shown in FIG. 5. Notice, in this regard, the reference axes X and Y, respectively; which lie in the plane of surface 70 and which are perpendicular to one another. The reflected portion 78 of the beams 72, 74 and 76, which is normal to the surface of the pad 70, is shown in FIG. 5 as lying along a reference axis Z. The reference axes X, Y and Z are mutually perpendicular to one another. The blue LED 66 lies in the YZ plane while the blue LED 68 lies in the XZ plane.

As is the case with regard to the two previously explained examples of our invention, the optical and electronic systems of the present example are adapted for packaging within a highly portable, hand held housing such as that shown at 6 in FIGS. 1-2. The electronic logic of the reflectometer of the present example is shown in FIGS. 6-7. The photodetector 84 is a diode of conventional type which generates a d.c. output current signal on a line 90 (FIG. 7) which is proportional to the intensity of the blue wavelength light impinging thereon as reflected normal to the paper pad 70 and as passed through the lens 77 and the filters 80 and 82 (FIG. 5). The d.c. current signal on line 90 is fed to a two stage amplifier circuit 86a, b. The first stage 86a is a transconductance amplifier which acts as a current-to-voltage converter which feeds the second stage 86b, the latter being a voltage amplifier. A voltage output signal from the amplifier circuit 86b is fed through a line 92 to a liquid crystal diode register 88 for visual display of the brightness of the pad 70.

The circuit of FIG. 7 contains a 2.5 volt d.c. bias circuit, generally designated 94, and an indexing circuit 96 which can be adjusted so that the register 88 will display all zeros when the output signal from the current-to-voltage converter 86a, as applied to the voltage amplifier stage 86b, does not exceed 2.5 volts d.c. Also included is a low battery voltage detector circuit 98 which includes a transistor 100 which turns on to initiate a low battery voltage indicator in the register 88 when the transistor 102 switches off at a selected threshold value, indicative of a low d.c. battery voltage of about 6.0 volts or less from a nominal 9.0 volt battery 104. The battery 104 provides power to operate a 5.0 volt d.c. regulator and filter circuit 106 which, in turn, powers all the active devices in the circuit of FIG. 7 when a two-position ON/OFF switch 108 is placed in the "ON" position as shown in that figure. The two blue LED's 66 and 68 are operated by means of a constant current source circuit 110 which includes a dual operational amplifier designated 112a and 112b.

The ultraviolet light source, which in this example is a fluorescent lamp 64, is operated by an ultraviolet light level feedback circuit 114 which includes an adjustable d.c. voltage regulator 116 powered by the battery 104 when a UV circuit ON/OFF switch 118 is placed in an "ON" position as shown in FIG. 7. The regulator 116, in turn, drives a voltage multiplier circuit 120, which, in turn, provides operating potential to the UV light source 64. A portion of the light emitted by the lamp 64 can thus be directed upon those paper samples whose brightness is to be measured which contain ultraviolet light excitable substances and which radiate blue light when thus excited. Another portion of the ultraviolet light emitted by the lamp 64, however, is detected by an ultraviolet light sensing diode 122, a corresponding d.c. output signal from which drives a current-to-voltage converter 124 which, in turn, drives a voltage amplifier 126 which, in turn, drives an adjustable error detecting comparitor circuit 128. An output signal from the comparitor circuit 128 is fed via a line 130 to the regulator 116 to complete an ultraviolet light level feedback circuit 114 (FIG. 6) operated by the photodetector 122 and includes the converter 124, amplifier 126 and error detector 128. A biasing circuit 132 is also included and provides an approximate 1.0 volt d.c. bias to render the amplifier 126 non-conductive for input signals presented thereto from the converter 124 which do not exceed that value.

Certain parts of the circuits of the photodetector 84 and amplifier 86 are electrically grounded to a single common ground location. In FIG. 7, these single position electrical grounds are indicated by a small triangle 133, as for example, that shown connected to the photodetector 84. These common grounds 133 are only necessary in the photodetector 84, and circuits 86a, 86b, 94 and 96 and upon the ground side of a capacitor 145 attached to the 5.0 vdc output terminal of the voltage regulator 190. The remaining electrical grounds of the circuit may, but need not necessarily, be connected to the same ground point and are designated in the conventional manner as, for example, at 135 on the voltage multiplier 120.

To complete the present example, the following table is provided below which identifies the various components comprising the circuit of FIG. 7.

| COMPONENT | DESCRIPTION |
| --- | --- |
| Blue LEDs 66, 68 | Ledtronic L200CWB5 |
| Photodetectors 84, 122 | Silicon Detector SD-172-12-12-221 |
| Capacitors 134 | 0.1 mfd |
| Capacitors 136 | 100 pfd |
| Capacitors 138 | 0.33 mfd |
| Capacitors 140 | 0.01 mfd |
| Capacitors 142 | 10 mfd |
| Capacitors 144 | 22 mfd |
| Capacitors 145 | 100 mfd |
| Resistors 146 | 200K Ohm |

-continued

| COMPONENT | DESCRIPTION |
| --- | --- |
| Resistors 148 | 20K Ohm |
| Resistors 150 | 0-100K Ohm Pot. |
| Resistors 151 | 1.5K Ohm |
| Resistors 152 | 73.2K Ohm |
| Resistors 156 | 4.32K Ohm |
| Resistors 158 | 0-1.0K Ohm Pot. |
| Resistors 160 | 475K Ohm |
| Resistors 162 | 49.9K Ohm |
| Resistors 164 | 1.21K Ohm |
| Resistors 166 | 100 Ohm |
| Resistors 172 | 10K Ohm |
| Resistors 174 | 39.2K Ohm |
| Resistors 176 | 54.9K Ohm |
| Resistors 178 | 5.62K Ohm |
| Resistors 180 | 100K Ohm |
| Resistors 182 | 681 Ohm |
| Resistors 186 | 1K Ohm |
| Resistors 188 | 0-50K Ohm Pot. |
| Operational Amplifiers 154 | Linear Technology LT1008CN |
| Op. Amps. 112a, b and 170a, b | National Semiconductor LM358N, Dual |
| Liquid Xtal display 88 | Martel Electronics DPM 100S |
| Operational Amplifiers 120 and 184a, b, c, d | National Semiconductor LM324, Quad |
| Transistors 100, 102, and 168 | Motorola 2N3904 |
| Regulator 116 | Linear Technology LM317T, 5.0 volts d.c. |
| Regulator 190 LP2950CZ, 5.0 volts d.c. | National Semiconductor |
| Blue Wavelength filter 82 | Kopp Glass Model 5-58, ½ peak height bandwidth of 60 nm wavelength centered on 457 nm wavelength |
| UV light absorbing filter 80 | Hoya Ltd., Model L-42 |
| UV transparent filter 75 | Pair of glass filters in line, one being a Hoya Ltd. UV 350 and the other being a Hoya Ltd. C-500 |
| Voltage Multiplier 120 | TDK CXA-L10L |

Although the present invention has been shown and described with respect to specific details of certain preferred embodiments thereof, it is not intended that such details limit the scope of this patent other than as specifically set forth in the following claims.

We claim:
1. A reflectometer for measuring optical brightness of a material comprising
 a housing including a surface member having a flat portion which defines an aperture for the uninterrupted passage of a collimated light beam therethrough, said flat portion being placable flush against a surface of a material whose brightness is to be measured,
 a first blue wavelength visible emitting diode disposed in said housing so as to direct a first collimated beam of blue light through said aperture onto said material at a first preselected angle relative to a plane parallel to said flat aperture defining portion of said member,
 receiving means disposed in said housing for receiving the portion of said blue light beam which is reflected through said aperture from said material at a second preselected angle relative to said plane, one of said preselected angles being essentially 90 degrees and the other being greater than zero and less than ninety degrees, and
 sensing means responsively connected to said receiving means for sensing the magnitude of the re- flected portion of said light beam relative to a predetermined standard.

2. The reflectometer of claim 1 wherein said member comprises a flat plate hingably connected to said housing.

3. The reflectometer of claim 1 wherein said aperture is circular.

4. The reflectometer of claim 1 wherein the other of said preselected angles is essentially 45 degrees.

5. The reflectometer of claim 1 wherein said first preselected angle is essentially 45 degrees relative to said plane and said second preselected angle is essentially 90 degrees relative to said plane.

6. The reflectometer of claim 1 wherein said receiving means comprises a silicon photocell.

7. The reflectometer of claim 1 wherein said sensing means is disposed in said housing.

8. The reflectometer of claim 1 wherein said receiving means comprises a device for converting light energy received thereon into electrical energy, said sensing means comprising
   amplifier means responsively connected to said receiving means for amplifying the electrical energy generated by said receiving means, and
   means for visually displaying data responsively connected to said amplifier means for generating a visual display in response to said electrical energy amplified by said amplifier means which is representative of the magnitude of the reflected portion of said light beam received by said receiving means as compared with said standard.

9. The reflectometer of claim 1 further comprising a blue optical filter disposed in said housing between said aperture and said receiving means such that the reflected portion of said light beam passes through said filter before being received by said receiving means.

10. The reflectometer of claim 1 further comprising ultraviolet light emitting means disposed in said housing so as to direct a quantity of ultraviolet light through said aperture onto said material at a third preselected angle relative to said plane.

11. The reflectometer of claim 1 further comprising a second blue wavelength visible light emitting diode disposed in said housing so as to direct a second collimated beam of blue light through said aperture onto said material at said first preselected angle relative to said plane, said second diode being disposed such that said second blue light beam is directed through said aperture along a path parallel to said plane which is rotatably displaced essentially 90 degrees from the path of said first blue light beam as measured parallel to said plane.

12. The reflectometer of claim 10 wherein said third angle is essentially equal to said first angle.

13. The reflectometer of claim 10 further comprising negative feedback means responsive to the intensity of ultraviolet light emitted by said ultraviolet light emitting means and operatively connected to said ultraviolet light emitting means for maintaining the intensity of the ultraviolet light emitted by said ultraviolet light emitting means at an essentially constant level.

14. The reflectometer of claim 10 further comprising a filter which is transparent with respect to ultraviolet light but which is otherwise opaque disposed between said ultraviolet light emitting means and said aperture.

15. The reflectometer of claim 10 wherein said ultraviolet light emitting means comprises a fluorescent lamp.

16. The reflectometer of claim 11 wherein said member comprises a flat plate hingably connected to said housing.

17. The reflectometer of claim 11 wherein said aperture is circular.

18. The reflectometer of claim 11 wherein the other of said preselected angles is essentially 45 degrees.

19. The reflectometer of claim 11 wherein said first preselected angle is essentially 45 degrees relative to said plane and said second preselected angle is essentially ninety degrees.

20. The reflectometer of claim 11 wherein said receiving means comprises a silicon photodetector.

21. The reflectometer of claim 11 wherein said sensing means is disposed in said housing.

22. The reflectometer of claim 11 wherein said receiving means comprises a device for converting light energy received thereon into electrical energy said sensing means comprising
   amplifier means responsively connected to said receiving means for amplifying the electrical energy generated by said receiving means, and
   means for visually displaying data responsively connected to said amplifier means for generating a visual display in response to said electrical energy amplified by said amplifier means which is representative of the magnitude of the reflected portion of said light beam received by said receiving means as compared with said standard.

23. The reflectometer of claim 11 further comprising a blue optical filter disposed in said housing, said blue filter being disposed between said receiving means and said aperture such that the reflected portions of said first and second light beams pass through said blue filter before being received by said receiving means.

24. The reflectometer of claim 11 further comprising ultraviolet light generating means disposed in said housing so as to direct a collimated beam of ultraviolet light through said aperture onto said material at a third preselected angle relative to said plane, said third preselected angle being essentially equal to said first preselected angle, said second preselected angle being essentially ninety degrees relative to said plane and said first and third preselected angles being greater than zero and less than ninety degrees relative to said plane.

25. The reflectometer of claim 24 further comprising a first ultraviolet light transmitting, visible light absorbing filter disposed between said ultraviolet light generating means and said aperture.

26. The reflectometer of claim 24 wherein said ultraviolet light generating means comprises a fluorescent lamp.

27. The reflectometer of claim 25 comprising an ultraviolet light limiting filter disposed between said aperture and said receiving means, which is opaque to ultraviolet light but otherwise transparent to blue light, for isolating said receiving means from ultraviolet light.

28. A reflectometer for measuring a reflective property of a material comprising
   a housing,
   a member attached to said housing having a flat aperture defining surface portion, said flat aperture defining portion being placeable flush against a surface of a material whose reflective property is to be measured,
   first blue wavelength visible light emitting means disposed in said housing so as to direct a first collimated beam of blue light through said aperture onto said material at a first preselected angle relative to a plane parallel to said material surface, second blue wavelength visible light emitting means disposed in said housing so as to direct a second collimated beam of blue light through said aperture onto said material at essentially said first preselected angle relative to said plane, the path of said second beam parallel to said plane, being rotationally displaced essentially 90 degrees from the path of said first beam which is parallel to said plane, receiving means disposed in said housing for receiving the portions of said blue light beams which are reflected through said aperture from said material at a second preselected angle relative to said plane, one of said preselected angles being essentially ninety degrees relative to said plane and the other being greater than zero and less than ninety degrees relative to said plane, and sensing means responsively connected to said receiving means for sensing the magnitude of blue light reflected from and generated in said material as received by said receiving means relative to a predetermined standard.

29. The reflectometer of claim 28 wherein each said first and second blue wavelength visible light emitting means comprises a separate blue wavelength light emitting diode.

30. The reflectometer of claim 28 wherein each said first and second blue wavelength visible light emitting means comprises a separate visible light source, each said source being adapted to generate a different collimated light beam, each said beam containing a blue wavelength component, and a blue optical filter disposed in said housing, in the path of said reflected blue light beam portions for passing a beam of blue light therethrough of relatively narrow bandwidth and for absorbing the remaining components of each of said light beam portions which have wavelengths outside of said bandwidth.

31. A reflectometer for measuring the optical brightness of a fiber containing material comprising a first blue LED for directing a first collimated beam of blue light onto a sample of fiber containing material at a first preselected angle relative to a surface of said sample, a second blue LED for directing a second collimated beam of blue light onto said sample in the same location as said first beam at said first angle relative to said surface, the direction of said second beam along the plane of said sample being rotationally displaced upon said plane essentially ninety degrees from the direction of said first beam along said plane, a constant current power source operatively connected to said first and second blue LED's, ultraviolet light source means for directing ultraviolet light onto said sample at said location, first photodetector means for receiving a portion of the light reflected from said sample at a second preselected angle relative to said surface, and for generating a first electrical output signal corresponding to the intensity of the light impinging on said first photodetector, second photodetector means for receiving a portion of the ultraviolet light generated by said ultraviolet light source and for generating a second electrical output signal corresponding to the intensity of said ultraviolet light portion, a regulated power source operatively connected to said ultraviolet light source means, negative feedback means responsively associated with said second photodetector means and operatively connected to said regulated power source for maintaining the ultraviolet light output intensity of said ultraviolet light source means at an essentially constant value, and means responsively connected to said first photodetector for sensing the intensity of said first electrical signal indicative of the optical brightness of said sample.

32. The reflectometer of claim 31 further comprising a voltage multiplier circuit responsively connected to said negative feedback means and operatively connected to said ultraviolet light source means.

* * * * *